United States Patent
Bardsley et al.

[11] Patent Number: 6,004,310
[45] Date of Patent: Dec. 21, 1999

[54] MULTILUMEN CATHETER SHAFT WITH REINFORCEMENT

[75] Inventors: Earl Bardsley, Newton; Kevin Gilmartin, Marsh Field, both of Mass.

[73] Assignee: Target Therapeutics, Inc., Fremont, Calif.

[21] Appl. No.: 09/098,671

[22] Filed: Jun. 17, 1998

[51] Int. Cl.$^6$ ............................ A61M 25/00
[52] U.S. Cl. .................. 604/524; 604/526; 604/527
[58] Field of Search .................. 604/264, 280, 604/523, 524, 526, 527, 282; 138/118, 123–125, 129, 132, 133, 134, 137, 138, 144, 153

[56] References Cited

U.S. PATENT DOCUMENTS

| | | |
|---|---|---|
| 2,407,929 | 9/1946 | Jeckel ............................ 340/850 |
| 2,437,542 | 5/1948 | Krippendorf . |
| 2,472,484 | 6/1949 | Krippendorf . |
| 2,472,485 | 6/1949 | Krippendorf . |
| 3,416,531 | 12/1968 | Edwards . |
| 3,485,234 | 12/1969 | Stevens . |
| 3,498,286 | 3/1970 | Polanyi . |
| 3,924,632 | 12/1975 | Cook . |
| 4,425,919 | 1/1984 | Alston, Jr. et al. . |
| 4,498,473 | 2/1985 | Gereg . |
| 4,739,768 | 4/1988 | Engelson . |
| 4,817,613 | 4/1989 | Jaraczweski et al. . |
| 4,899,787 | 2/1990 | Ouchi et al. . |
| 5,063,018 | 11/1991 | Fontirroche et al. . |
| 5,190,520 | 3/1993 | Fenton, Jr. et al. . |
| 5,221,255 | 6/1993 | Mahurkar et al. . |
| 5,454,795 | 10/1995 | Samson ............................ 604/527 |
| 5,460,608 | 10/1995 | Lodin et al. ....................... 604/96 |
| 5,538,512 | 7/1996 | Zenzon et al. ..................... 604/508 |
| 5,542,937 | 8/1996 | Chee et al. . |
| 5,603,991 | 2/1997 | Kupiecki et al. . |
| 5,695,483 | 12/1997 | Samson . |
| 5,782,811 | 7/1998 | Samson et al. ..................... 604/527 |

*Primary Examiner*—Wynn Wood Coggins
*Assistant Examiner*—LoAn H. Thanh
*Attorney, Agent, or Firm*—Morrison & Foerster LLP

[57] ABSTRACT

This invention is a surgical device. In particular, this invention is directed to a multilumen catheter for accessing the vascular system of a body. The multilumen catheter includes a catheter shaft, at least a portion or which includes at least one lumen reinforced with a support member which may include a polymeric or metallic braid, coil or knit material. The reinforced lumen may further include a thin-walled liner or coating of lubricious material. The reinforced lumen may have a circular cross-section adapted to receive a guidewire. The interior surface of the reinforced lumen may have a smooth and continuous surface or a non-uniform surface.

20 Claims, 3 Drawing Sheets

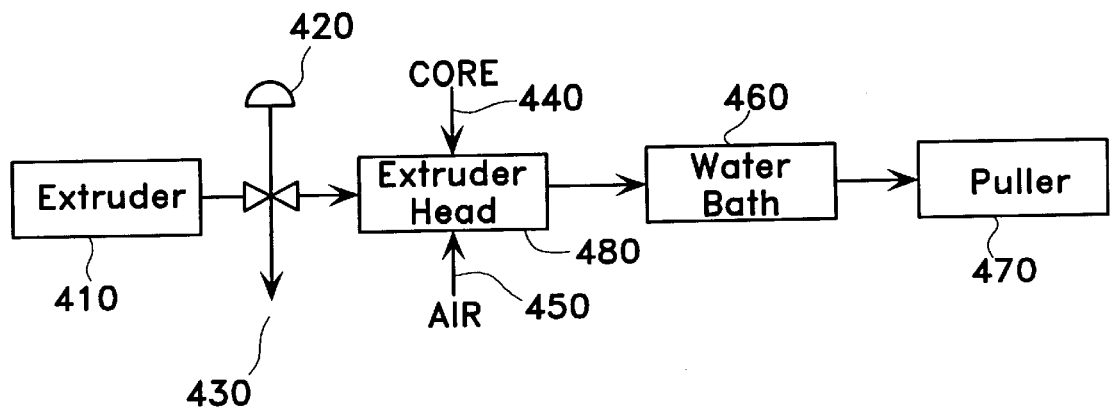
FIG. 6
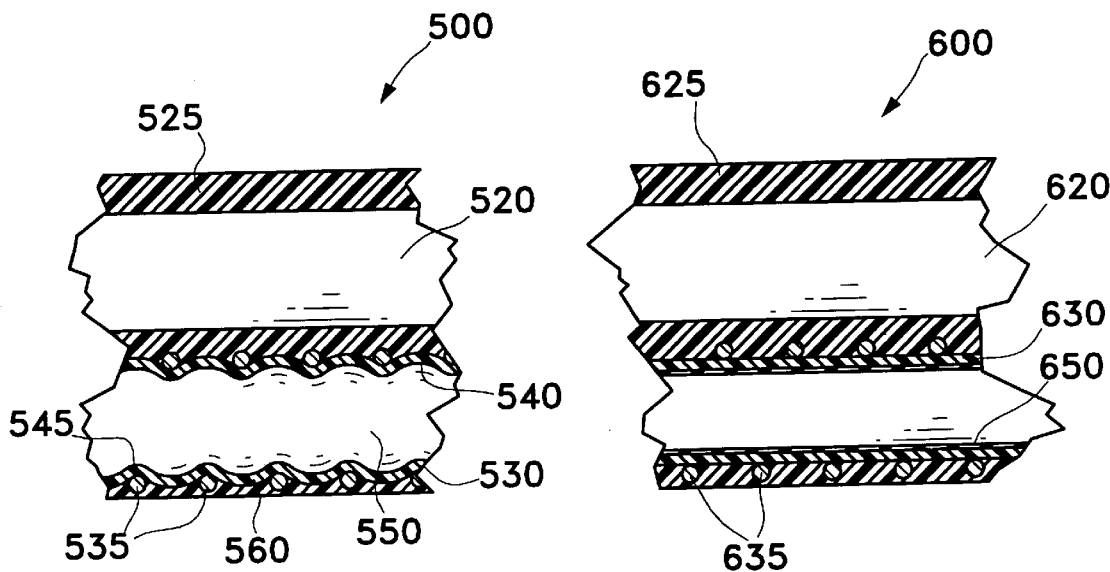
FIG. 7
FIG. 8

MULTILUMEN CATHETER SHAFT WITH REINFORCEMENT

FIELD OF THE INVENTION

This invention is a surgical device. In particular, this invention is directed to a multilumen catheter accessing the vascular system of a body. The multilumen catheter includes a catheter shaft, at least a portion or which includes at least one lumen reinforced with a polymeric or metallic braid, coil or knit material and may further include a liner or coating of lubricious material.

BACKGROUND OF THE INVENTION

Catheters are used in a variety of procedures to treat vascular maladies throughout the body. Catheters are used to place various treatment materials, drugs, and devices within remote regions of the human body. Catheters with distal balloons are used to treat narrowed regions in the arterial system via percutaneous transdermal angioplasty (PCTA) by expanding the balloon in the region of the plaque narrowing a vessel lumen and pressing the plaque into the vessel wall.

Often, the target which one desires to access by catheter is within a soft tissue such as the liver or brain. Such sites are extremely difficult to reach by way of the vasculature system because the remote arterial pathways are increasingly narrow and have tortuous pathways with sharp bends or curves often winding back on themselves.

Catheters designed to traverse such pathways must provide the desired balance between the flexibility required to allow passage of the catheter tip through the sharp bends of the increasingly narrow blood vessels and the stiffness required to allow sufficient pushability and torqueability as the catheter is inserted into the body and advanced through the tortuous pathways. It is commonplace for modern high performance catheters to have a number of sections of different flexibilities along its length.

In many cases, the catheter is designed to be used as a unit with a torqueable guidewire. The guidewire is typically bent at its distal end and may be guided by rotating and advancing the wire along a tortuous, small vessel pathway, to a target site. The catheter is constructed to slide over the guidewire and traverse the path established by the guidewire. Typically the guidewire and catheter are advanced along the tortuous pathway by alternately advancing the wire along a region of the pathway, then advancing the catheter axially over the advanced wire portion. Further details on the problems and an early, but yet effective, catheter designed for such traversal may be found in U.S. Pat. No. 4,739,768 to Engelson.

One problem that may be encountered as the guidewire and catheter are advanced as described above, is that the guidewire can become stuck or jammed against the internal tubular surface or walls of the lumen. This problem is caused, at least in part, by the distortion of lumen walls against the guidewire, unfavorable friction properties between the guidewire and the lumen surfaces, and/or unfavorable geometrical positioning of the guidewire relative to the inner surfaces of the catheter lumen. Typically, the problem arises when a sharp bend is encountered or where two or more sharp bends occur in succession. When the catheter and wire become locked together in this manner it may be impossible to either advance or withdraw the wire relative to the catheter. In such cases, the wire and catheter must be withdrawn together until both are straight enough to allow the wire to be moved freely axially within the catheter, and often, it may not then be possible to reach the targeted site. This same problem may be encountered when other types of instruments (i.e., an angioscope) is advanced through a catheter lumen.

In a number or procedures, it may be necessary that the catheter have two or more lumens extending within at least a portion of the catheter shaft. For example, the catheter may have one lumen adapted for use with a guidewire to position the catheter, and one or more additional lumen for balloon inflation or deflation, irrigation, delivery of drugs or other treatments, or to facilitate the insertion of other surgical devices, such as for example, an angioscope. The lumen employed may have any suitable cross-sectional shape as required for the particular use.

Such multilumen catheter designs are particularly susceptible to kinking or ovalization of the cross-sectional shapes of the various lumen when the catheter is exposed to high flexure or high torsion, such as when the catheter is traversed through the bends in the vasculature. While a certain small amount of distortion of the interior cross-sectional shapes of a lumen may be acceptable in some applications, such distortions of the interior shapes of the lumen may result in a lumen being kinked or closed off or may result in the wall of the lumen being forced against any element that has been inserted into the lumen as described above. For example, ovalization of a normally round shaped guidewire lumen causes the lumen walls to pinch the guidewire thus prohibiting free relative movement between the guidewire and the guidewire lumen. Multilumen catheters known in the art do not tend to provide a suitable shaft design to ensure the free relative movement of an element (i.e., a guidewire) placed within a guidewire lumen.

While some of these disadvantages may be somewhat alleviated by increasing the thickness of the catheter lumen walls, it is not desirable to do so for a number of reasons. Increased wall thickness may adversely decrease flexibility, increase the overall size of the catheter profile, or decrease the internal space available for necessary lumens. In addition, increased wall thicknesses typically result in increased mass. Increased mass increases the tendency of the catheter to force the guidewire out of a bent or curved configuration as the catheter is advanced over the guidewire. This may be critical in the distal tip region of some over-the-wire catheters because a relatively low mass at the distal tip region of the catheter may be necessary for tracking the catheter over the increasing flexible guidewires necessary to access the more tortuous vascular pathways.

To some extent, the problem of catheter collapse has been addressed in multilumen hemodialysis catheter designs using a reinforced construction. For example, U.S. Pat. 5,190,520 to Fenton, Jr. et al. discloses a reinforced dual lumen catheter having a cylindrical portion with a central axis and a substantially rectangular divider within the cylindrical portion which defines two internal D-shaped lumens. A wire reinforcement filament is embedded in the cylindrical portion in a helical pattern about the central axis. The reinforced multilumen catheter disclosed in U.S. Pat. No. 5,221,255 to Mahurkar et al. discloses similar cylindrical tube having a septum extending therein which defines two D-shaped lumens. To minimize kinking the catheter has a spiral of relatively stiff material embedded in the cylindrical wall of the catheter which tends to hold the outer wall of the catheter in a cylindrical shape. The catheter further has a reinforcing member extending along the full length of at least one of the lumens, preferably the reinforcing member is embedded in the septum.

An extrusion method for producing a reinforced multilumen tubing is disclosed in U.S. Pat. No. 5,063,018 to Fontirroche et al. The disclosed extrusion method involves first extruding an inner tube over a wire mandrel, adding a braided tube if desired, and then extruding an outer tube over the inner braided tube. The wire mandrel forms a first lumen within the braided tube and a second lumen is formed in the outer tube during extrusion. Of course, the resulting tubing construction is limited to materials which are suitable for extrusion and to tubing sizes and thicknesses obtainable by the extrusion process.

None of these constructions, however, provide a low-profile, high flexibility catheter shaft having a reinforced lumen which resists cross-sectional distortion and provides for free axial movement of an inserted element relative to the lumen as the catheter device is advanced through the curves and sharp bends of a vascular pathway as described in detail below. Further, none of these devices have a reinforced lumen having a low profile, low mass, low friction construction as described below.

SUMMARY OF THE INVENTION

This invention is a multilumen catheter shaft section having use in wide array of catheter designs. The catheter shaft section generally includes a tubular elongate outer shaft member defining at least a first lumen, a tubular inner shaft member disposed within the outer shaft member defining a second lumen generally parallel to the first lumen, and a support member generally concentric with and exterior to said tubular inner shaft member.

The tubular inner shaft member may be of a relatively thin walled construction. In one embodiment the tubular inner shaft member has a wall thickness of less that about 0.001 inches, more preferably less that about 0.0005 inches. The tubular inner shaft member may be made from any suitable biologically compatible material, but preferably is made from a low-friction or lubricious material. In one embodiment, the tubular inner shaft member comprises PTFE, FEP, or their mixtures.

The tubular outer shaft member may be made from any suitable biologically compatible material. In one embodiment, the tubular outer shaft member comprises nylon, Pebax, polyethylene, polypropylene, polyvinylchloride, polyurethane, silicone, or their blends, alloys, and copolymers The support member may comprise a polymeric or metallic braid, coil or knit material. In one embodiment the support member comprises a braided material, preferably of polymeric fibers. The braided material may also include metallic wires or ribbons. A braided support member generally has a braid of discrete braid elements (such as, for example, fibers, wires, ribbons, threads, etc.) having interstices between the discreet braid elements, the exact configuration of which depends upon the braid or winding pattern. The support member may instead comprise a spirally wound material. In one aspect of the present invention, the support member has an outside diameter of less than about 0.050 inches.

The second lumen generally comprises an interior surface. In one embodiment, the interior surface is substantially smooth and continuous and may further include an optional hydrophilic coating. The interior surface of the second lumen may comprise a non-uniform surface. The non-uniformities may take the form of alternating high regions and low regions. In one aspect of the present invention, the desired non-uniformities are formed as the tubular inner shaft member conforms to the profile of the braided support member.

BRIEF DESCRIPTION OF THE DRAWINGS

FIG. 6 is a diagrammatic representation of the an extrusion process suitable for producing a multilumen catheter shaft.

FIG. 7 shows a longitudinal cross-section of a catheter shaft having a non-uniform inner lumen surface according to the present invention.

FIG. 8 shows a longitudinal cross-section of a catheter shaft having a inner coating according to the present invention.

DESCRIPTION OF THE INVENTION

This invention is a catheter shaft section having a reinforced lumen and a catheter incorporating such a section. The reinforced lumen may incorporate a section constructed to have structural features which aid in preventing the sticking or locking of the internal walls surfaces of the lumen against any element positioned for relative movement within the lumen. The catheter shaft section may be a multilumen device having at least one reinforced lumen constructed to aid in preventing the sticking or locking of the internal surfaces of the lumen against an element positioned for relative movement within the lumen. The invention includes the method of making the catheter shaft sections.

Figure 1:
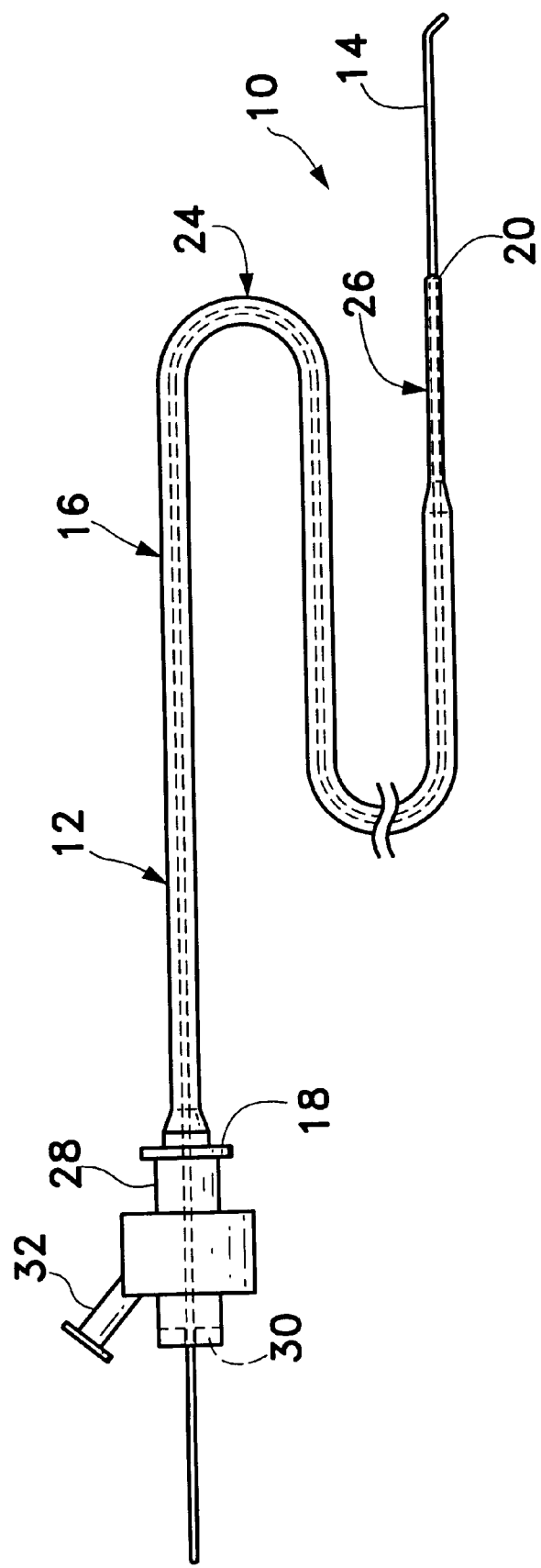
FIG. 1 shows a catheter device, including a catheter having a catheter shaft section constructed according to the principles of the present invention.

A typical catheter device 10 which may incorporate the concepts of this invention is shown in FIG. 1. The device includes a catheter 12 in the form of an elongated tubular member which will be described below, and a guidewire 14. The catheter device is designed for accessing a target site which can be reached only along a small tunnel-like pathway. The catheter 12 includes an elongate outer tubular surface 16 having proximal end 18 connected to fitting 28 and distal end 20. The area inside tube 12 has one or more longitudinal hollow areas or lumen extending between the two ends. Fitting 28 is constructed to allow guidewire 14 to pass through and may optionally include seal 30 to prevent leakage around the guidewire while still allowing the guidewire to be rotated and advanced relative to the catheter as required during use. Fitting 28 may also include bifurcated port 32 which may be used to access one or more of the catheter lumens.

The tubular member 12 can be between about 50–300 cm in length, and is typically and more preferably between about 100–200 cm in length. The guidewire is positioned in a lumen that is typically between about 1–7 mils (1 mil is equal to 0.001 inch) greater than the diameter of the guidewire. Additional lumen for a variety of purposes known in the art may or may not be provided. The lumen or lumens may have a substantially uniform cross-sectional area along its length or may vary along the catheter length.

A typical catheter device may include a number of sections having different structural characteristics along its length. Catheter or tubular member 12, for example, is shown having a proximal or first section 24 and a relatively more flexible distal section 26 terminating at distal end 20. Typically, proximal segment 24 makes up between about 70–90% of the total length of tubular member 12, and relatively flexible distal segment 26 makes up the remaining 10%–30% of the length.

The catheter device may have a number of lumen configurations including both single lumen configurations and multilumen configurations. It is desirable for such catheter devices to have a shaft portion which is constructed to allow the lumen to maintain its cross-sectional shape during its intended use, provide an internal lumen structure that does not inhibit free axial movement of any element positioned therein, and yet maintains the desired flexibility, pushability, torqueability and low profile required for its intended use. To this end, a catheter shaft having a reinforced lumen and an internal lumen structure which allows axial movement of a longitudinal element within the lumen using minimal force is described below. Although the invention is not intended to be so limited, the examples discussed below are directed to multilumen catheter shaft configurations.

Figure 2:
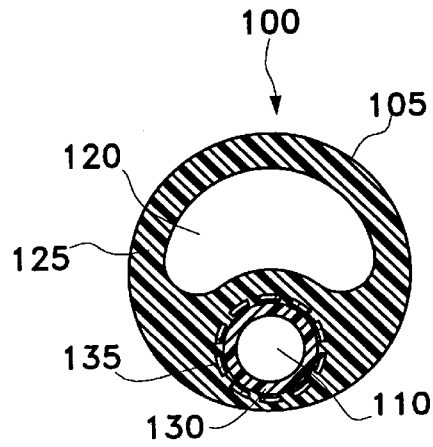
FIGS. 2 and 3 show, respectively, transverse and longitudinal cross-sectional views of a catheter shaft section made according to the principles of the present invention.
Figure 3:
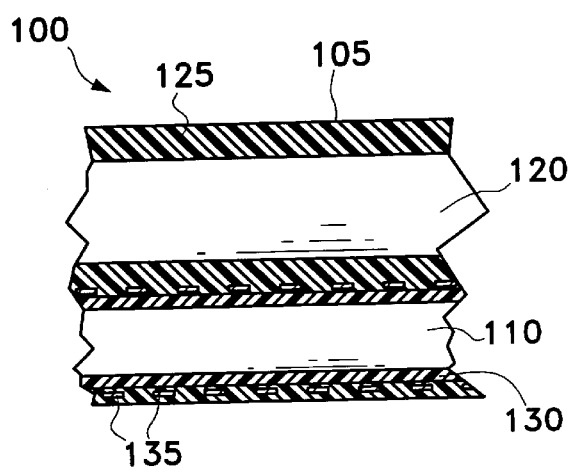

An exemplar multilumen catheter construction made according to the principles of the present invention is shown in cross-section in FIGS. 2 and 3. At least a section of catheter 100 is constructed to have outer member 125 having outer tubular surface 105, inner member 130, and support member 135. Inner member 135 defines lumen 110 which has a generally circular cross-sectional shape as shown. Outer member 125 is preferably an extruded member having a main lumen 120 formed therein during extrusion. In a preferred embodiment, lumen 110 has a circular cross-sectional shape to accept a guidewire (such as guidewire 14 as discussed with reference to FIG. 1) or other longitudinal element. Main lumen 120 is shown having a crescent shape, but could be any desired shape suitable for balloon inflation/deflation, infusion of drugs or other fluids, or delivery of other surgical devices such as vaso-occlusive coils, angioscopes, etc. The lumens may have a substantially uniform cross-sectional area along their length, or may vary along the catheter length, for example the distal end may taper toward a smaller diameter in a direction away from the proximal end.

Outer member 125 may be made from any suitable biologically compatible catheter material or may be extruded from a number of different materials along its length as described in U.S. Pat. No. 5,542,937 to Chee et al., the entirety of which is hereby incorporated by reference. Suitable polymers include thermoplastics such as nylon, Pebax, polyethylene, polypropylene, polystyrene, polyurethanes, polyethylene terephthalate, polyesters, polyvinyl chloride, silicone and lubricious polymers such as polyfluorocarbons or polysulfones.

Inner member 130 is of a relatively thin construction and, although many common biologically compatible polymers would be suitable, it is preferably made from a durable, lubricious material having a low coefficient of friction to minimize the magnitude of force required to slide the guidewire axially within lumen 110. Suitable polymers includes polyurethane, high density polyethylene (HDPE), low density polyethylene (LDPE), polyvinylchloride, fluoropolymers including PTFE, FEP, vinylidene fluoride, and their mixtures, alloys, copolymers, and block copolymers. Most preferably, inner member 130 is made from PTFE, FEP, or their mixtures. The wall thickness of the material and its specific properties may depend in part upon whether the catheter shaft portion is proximally located on the catheter device (thus requiring more stiffness) or distally located on the catheter device (thus requiring a flexible material of suitable softness and modulus of elasticity). It is may also be desirable to choose polymers for the inner member 130 and the outer member 125 which adhere to each other or are miscible with each other under appropriate conditions so that an optimum bond is obtained at the interface of the outer member 125, inner member 130 and support member 135. Although outer member 125 and inner member 130 are described generally as discreet elements, when the same polymers are used for both outer member 125 and inner member 130 the final product will be substantially unitary having only the support member 135 embedded therein.

The support member 135 may be of a variety of different materials and configurations designed to impart the desired stiffness to the catheter shaft section and in particular ensure that the cross-sectional shape of the lumen remains substantially undistorted as in undergoes the high flexure encountered during traversal of the sharp bends in the vascular pathway. The reinforcing and stiffening properties of the support member 135 allows the inner member to be extraordinarily thin walled and yet maintain the integrity of the lumen cross-sectional shape. Inner member 135 may be as thin as about 0.0002 inches, more preferably between about 0.0002 inches to about 0.001 inches, but may be as thick as about 0.010 inches or more depending on the desired overall flexibility of the catheter shaft portion. Most preferably, inner member 135 has a thickness of about 0.0005 inches or less.

Figure 4:
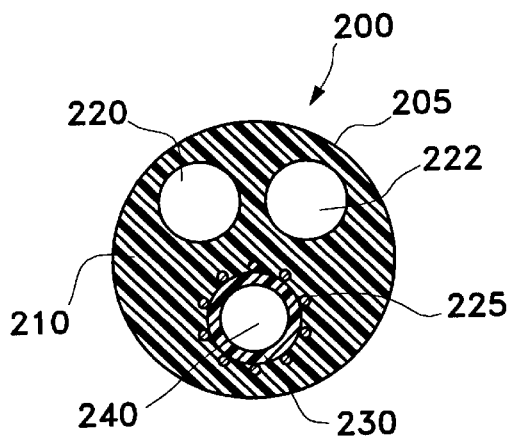
FIG. 4 shows a transverse, cross-sectional view of a catheter shaft having an alternate configuration.

Suitable support member constructions include metallic and non-metallic fibers, wires, and ribbons which may be configured in a single or multiple spirals, braids or knits as is known in the art. Support member 135 is shown generally as a ribbon material which may be a metallic material, such as super-elastic alloys or stainless steel, or non-metallic materials such as those made of polyaramids, carbon fibers, Dacron, Nylon, or liquid crystal polymer and may even be made using natural fibers such as silk and cotton. Specifics of spiral wound ribbon constructions suitable for this invention can be found, for example, in U.S. Pat. No. 5,695,483 to Samson, the entirety of which is herein incorporated by reference. Support member 225, as shown in FIG. 4, is shown generally of a wire or thread material which may be of any of the same materials. Support member 330 shows a preferred braided construction. Preferably the braid material is made of metallic or non-metallic wire, fiber or ribbons. In a preferred embodiment, support member 330 is braided polymeric fibers, most preferably liquid crystal polymer fibers. Different braid materials as well as winding densities may be employed along the length of the catheter shaft to allow the stiffness of the catheter device to be "tuned" according to the desired performance requirements.

One important aspect of this multilumen catheter shaft construction is that this construction allows support member 135 to be relatively small in diameter compared to the diameter of the catheter as a whole. When lumen 110 is configured to receive a guidewire, the support member concentrically disposed about the inner member will preferably have an outside diameter of about 50 mil or less, preferably about 10 mil to about 35 mil. This allows maximum lumen integrity surrounding the guidewire while allowing the catheter shaft portion as a whole to remain quite flexible. The small diameter support member 135 also allows for reduced mass in the area of the distal tip which enhances the ability of the catheter to track over a tortuous vascular pathway established by the guidewire. The ability of lumen 110 to maintain its original circular cross-sectional shape during use minimizes the potential that the lumen walls would be distorted or deflected against the guidewire. Such lumen distortion or deflection would inhibit free relative motion of the guidewire within lumen 110.

Another important aspect of this catheter shaft construction is that inner member 130 is a very thin walled construction. This allows the use of materials having superior frictional properties to be selected with only minimal effect on the stiffness as compared to thicker walled constructions that would preclude the use of certain stiffer materials because of the stiffness effects of a thicker walled construction. In addition, minimizing the thickness of inner member 130 likewise reduces the overall diameter of the support member 135 resulting in the advantages described above. Accordingly, inner member 130 preferably has a thickness of about 0.00075 inches or less, more preferably about 0.0005 inches or less.

As mentioned above, the multilumen catheter shaft using the principles of the present invention may be constructed with any number of suitable lumen shapes and configurations tailored to the requirements of a particular application. For purposes of further example, FIG. 4 shows an alternate multilumen catheter shaft construction. Catheter 200 having outer tubular surface 205 is constructed from outer member 210, inner member 230, and support member 225. Inner member 230 defines lumen 240 which has a generally circular cross-sectional shape for accepting a guidewire. Outer member 210 is preferably an extruded member having a first lumen 220 and a second lumen 222. If desired, either or both of first lumen 220 and second lumen 222 could also be provided with a surrounding support member and or inner member to maintain the cross-sectional shape of the lumen and provide improved frictional properties.

Figure 5:
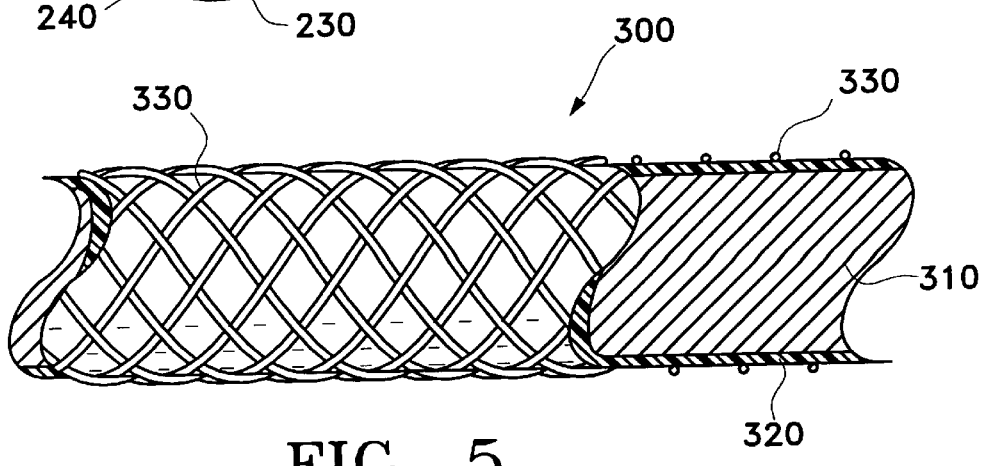
FIG. 5 shows an illustration in partial cross-section of a portion of the core element assembly used to make a multilumen catheter shaft according to the principles of the present invention.

The preferred method of making the multilumen shaft constructions as described above generally involves two steps. First, an inner core element is constructed and second, an outer member is extruded over the inner core element. FIG. 5 shows a preferred inner core element 300 which comprises mandrel wire 310, inner member 320, and support member 330 in the form of a braided wire or fiber. Inner member 320 is manufactured onto mandrel wire 310 by way of an extrusion, coating, spraying, or dipping process which allows a very thin, uniform layer to be placed over mandrel wire 310. Mandrel wire 310 may be coated and spooled for later feeding into the extruder. After inner member 320 is applied to mandrel wire 310, support member 320 is braided (or otherwise wound or applied) over inner member 320 by known conventional techniques. The resulting inner core element 300 can then be fed into an extruder to complete the multilumen catheter shaft assembly.

The inventive multilumen catheter shaft is preferably completed using an extruder of typical design and configuration shown schematically in FIG. 6. In this depiction, a conventional extruder 410 feeds an extruder head or die 480. The extruder may be of known design such as a screw extruder and use, for instance, screws typically chosen for the polymers selected to make the catheter shaft. The extruder 410 has a control valve 420 which can be operated either as a proportional valve or as a cut-off valve. The valve either supplies the polymer to the extruder head 480 or to a dump region 430, potentially for regrind or recycle. The inner core element 440 is supplied to a central orifice through the die in the extruder head. Air 450 is also supplied to the extruder head and is connected to each lumen being extruded. The purpose of air 450 is to ensure that the extruded lumen remains open until the molten plastic has had sufficient time to set. Alternatively, the lumen formed during the extrusion process could be created with full length wire mandrels, which would require subsequent removal.

The polymer from the extruder 410 enters the extruder head 480 and is applied in the desired shape over the inner core element 300. The assembly exits through the die face which forms the catheter shaft's final shape including any desired lumen. The semi-molten catheter shaft with inner core element 300 is then pulled through a water bath 460 typically using a puller 470. The mandrel wire portion of core element 300 is then removed.

This process of forming the inventive multilumen catheter shaft is particularly advantageous in that it allows for an extremely thin inner polymeric layer and allows long lengths of the inner core element to be spooled for continuous feeding into the extruder.

In addition, this manufacturing process makes it possible to structure the inside surface of the reinforced inner lumen in such a manner as to further reduce the amount of force required to advance a guidewire or other such element through the lumen. This is accomplished by creating a non-uniform interior lumen surface structure. An example of a catheter shaft section having such a structure is shown in cross-section in FIG. 7. Similar to the catheter shaft construction of FIGS. 2 and 3, catheter 500 has outer member 525 having main lumen 520 and inner member 560 which includes inner lumen 550 for receiving a guidewire or the like for axial movement therein. Support member 535, preferably in the form of a braided member as described above, is captured between outer member 525 and inner member 560.

As support member 535 was braided onto thin-walled inner member 560 in the manner described with reference to FIG. 5, the winding tension maintained in the braid resulted in a desirable deformation of inner member 560 as the inner member polymeric material deformed into and around the interstices of the braid material. Where the tension of the braid acted locally on the inner member 560, it created a non-uniform or structured inner surface having high regions 545 and low regions 540 corresponding to the geometry of the braid used. The ability to form these structural features is facilitated, at least in part, to the use of the thin-walled inner member construction. The application of heat to the inner core element may result in more pronounced structural features.

These structural features are important in that they lower the overall area of contact between the guidewire and the inner surface of lumen 550 and provide some ability to deflect normal forces which will be applied by the guidewire against the internal tubular surface so as to prevent jamming, sticking, or locking of the guidewire against the surface. When the guidewire is advanced within lumen 550 and contacts these structural features, the guidewire is deflected so that the guidewire does not provide substantial forces normal to the surface of the internal lumen wall and therefore does not become jammed or locked into position on the surface of the internal lumen wall, particularly when the catheter sections are sharply bent. These structural features in combination with the use of a proper low friction inner member material (i.e., PTFE or FEP), and a reinforced lumen construction to resist any distortion of the cross-sectional shape of the guidewire lumen results in a particularly desirable guidewire lumen for use in a flexible multilumen catheter shaft as herein described.

The frictional properties between the guidewire (or other inserted instrument or device) and the lumen walls may be further improved by the addition of an internal lubricious coating as shown in catheter 600 with reference to FIG. 8. Similar to the constructions above, catheter 600 has an outer member 625 defining main lumen 620 and an inner member 630 defining lumen 640. The interior of lumen 640 may be coated with a lubricous, preferably hydrophilic coating 650 by way of forcing the coating material into the lumen by pressure, or drawn in by gravity or vacuum. Examples of suitable coating materials may be found, for example, in U.S. Pat. No. 5,603,991 to Kupiecki et al. and U.S. Pat. No. 5,538,512 to Zenson et al., the entirety of both are herein incorporated by reference. Use of such coatings may allow the use of a wider range of inner member materials as their base lubricious properties will not be as critical.

While preferred embodiments of the invention have been described herein, it will be recognized that a variety of changes and modifications can be made without departing from the spirit of the invention as found in the appended claims.

We claim as our invention:

1. A multilumen catheter shaft section comprising an elongate tubular outer shaft member defining at least a first lumen, an elongate tubular inner shaft member disposed within said outer shaft member and defining a second lumen, said second lumen substantially parallel to and external to said first lumen, and a support member concentric with and exterior to said tubular inner shaft member, said tubular inner shaft member having a wall thickness of less than about 0.001 inches.

2. The catheter shaft section of claim 1, wherein the tubular inner shaft member comprises a polymer selected from the group consisting of PTFE, FEP, and their mixtures.

3. The catheter shaft section of claim 2, wherein said wall thickness of said tubular inner shaft member is less than about 0.0005 inches.

4. The catheter shaft section of claim 2, wherein the outer shaft member comprises one or more materials selected from the group consisting of nylon, Pebax, polyethylene, polypropylene, polyvinyl chloride, polyurethane, silicone, their blends, alloys, and copolymers.

5. The catheter shaft section of claim 1 wherein said support member comprises a braided material.

6. The catheter shaft section of claim 5, wherein said braided material comprises polymeric fibers.

7. The catheter shaft section of claim 5, wherein said braided material comprises a material selected from the group consisting of metallic wires and metallic ribbons.

8. The catheter shaft section of claim 1, wherein said second lumen comprises an interior surface which is substantially smooth and continuous.

9. The catheter section of claim 8, wherein at least a portion of said interior surface further included a hydrophilic coating.

10. The catheter shaft section of claim 1, wherein said second lumen comprises a non-uniform interior surface.

11. The catheter shaft section of claim 10 wherein said non-uniform interior surface comprises alternating high regions and low regions.

12. The catheter shaft section of claim 1 wherein said support member comprises a spirally wound material.

13. The catheter shaft section of claim 1 wherein said support member comprises a knit material.

14. The catheter shaft section of claim 1 wherein said support member has an outside diameter less than about 0.05 inches.

15. The catheter shaft section of claim 1, wherein said elongate tubular outer shaft member further defines a third lumen.

16. A multilumen catheter shaft comprising:
 a). a flexible elongate tubular outer shaft member defining a first lumen;
 b). an elongate tubular inner shaft member disposed within said outer shaft member, said tubular inner shaft member having an outer surface and an inner surface, said inner surface defining a guidewire lumen substantially parallel to and external to said first lumen;
 c). a support member concentric to and contacting said outer surface, said support member comprising a braid of discrete braid elements having interstices between said discreet braid elements; and
 d). said tubular inner shaft member conforming to the profile of the discreet elements and the interstices of said braid such that said inner surface is non-uniform.

17. The catheter shaft section of claim 16, wherein the tubular inner shaft member comprises a polymer selected from the group consisting of PTFE, FEP, and their mixtures.

18. The catheter shaft section of claim 7, wherein said tubular inner shaft member has a wall thickness of less than about 0.001 inches.

19. The catheter shaft section of claim 17, wherein the outer shaft member comprises one or more materials selected from the group consisting of nylon, Pebax, polyethylene, polypropylene, polyvinyl chloride, polyurethane, silicone, their blends, alloys, and copolymers.

20. The catheter shaft section of claim 16, wherein said elongate tubular outer shaft member further defines a third lumen.

* * * * *